United States Patent [19]

Gipson et al.

[11] 3,952,068

[45] Apr. 20, 1976

[54] VINYLIDENE ALCOHOL COMPOSITIONS

[75] Inventors: Robert Malone Gipson; John Gordon Milligan; Floyd Edward Bentley, all of Austin, Tex.

[73] Assignee: Jefferson Chemical Company, Inc., Houston, Tex.

[22] Filed: July 17, 1975

[21] Appl. No.: 596,885

Related U.S. Application Data

[62] Division of Ser. No. 472,427, May 22, 1974, abandoned, which is a division of Ser. No. 260,545, June 1, 1972, Pat. No. 3,887,624.

[52] U.S. Cl. ............................ 260/632 R; 252/8.9; 252/9; 260/638 R
[51] Int. Cl.$^2$.................. C07C 31/02; C07C 33/02
[58] Field of Search ............................... 260/632 R

[56] References Cited
UNITED STATES PATENTS 2,844,534   7/1958   Cottle et al. .................... 260/632 R

OTHER PUBLICATIONS

Landa et al., "Chem. Abstracts," Vol. 61 (1964), Cols. 15961,2 (15962f).

*Primary Examiner*—Joseph E. Evans
*Attorney, Agent, or Firm*—John R. Kirk, Jr.; James L. Bailey; Lee G. Meyer

[57] ABSTRACT

Particular compositions of vinylidene alcohols are provided which are distinguishably characterized by their structure, their biodegradable nature, and by their very low pour point characteristics. These compositions can be used to provide useful surfactants and detergents and to form distinctive ethoxylate derivatives having unusual attributes, such as biodegradability, very high rates of water solubility, nongelling tendencies, and superior wetting ability; and certain of these ethoxylate compositions are synergistic in wetting ability and, unlike related ethoxylates of conventional alcohols, the ethoxylates of certain compositions possess cloud point temperatures within an especially desired range.

2 Claims, No Drawings

VINYLIDENE ALCOHOL COMPOSITIONS

CROSS-REFERENCE TO RELATED APPLICATION

This application is a divisional of copending U.S. patent application, Ser. No. 742,427 filed May 22, 1974 now abandoned which in turn is a divisional of U.S. patent application, Ser. No. 260,545 filed June 7, 1972 now U.S. Pat. No. 3,887,624 which claims ethoxylate derivatives of the vinylidene alcohols herein claimed.

BACKGROUND OF THE INVENTION

1. Field of the Invention

This invention relates to the field of synthetic alcohols and to products useful for forming synthetic surfactants. Novel compositions exhibiting unusual characteristics and superior properties are included.

2. Description of the Prior Art.

Alcohols derived from both natural and synthetic origins have been widely utilized in a variety of applications. Exemplary areas in which such alcohols and their derivatives have been employed include their application in plasticizers, textile treatments, lubricants, polyurethanes, amines, alkyd coatings, surfactants, and the like. The employment of alcohols in the surfactant area is notably increasing in importance.

Surfactants, such as the alcohol alkoxylates, have been broadly employed by the detergent and other related industries, as wetting agents, solubilizing agents, washing agents, foaming agents, emulsifying agents, rewetting agents, dispersing agents, scouring agents, and the like. Since the various surfactant applications of such alcohols are so myriad and categorically nondistinctive, a more conveneint manner of characterizing the surfactants than by their utility is to use a system wherein they are classified as anionic, cationic, amphoteric, or nonionic, depending upon the nature of the ionic charge, if any, of the hydrophilic moiety of the surfactant.

Nonionic-type surfactants to which the subject invention is related have been derived from alcohols by condensing them with alkylene oxides. These, as well as the other surfactant types, may or may not exhibit a sufficient combination of properties so that they can be used beneficially in more than one application.

Regardless of whether a material has a rather wide or narrow range of useful functions, there are some relatively basic and cogent criteria that, in reality, can dictate the suitability and/or acceptability of an alcohol and its surfactant derivatives. For example, a synthetic surfactant may be an excellent detergent and wetter and yet not be biodegradable. This fact would, in effect, bar acceptability of this surfactant by the public and/or the industry.

In like manner, a surfactant may have excellent and varied activities but exist in such a physical state that its use is inconvenient, if not prohibited in many applications. Accordingly, the surfactant may, under conditions normal to its application, undergo gelling and thus become an unusable product. The product may have a prohibitive slow rate of solution in water or have an undesirable cloud point, whereby the value of the surfactant is substantially diminished.

The possession of such attributes as biodegradability, nongelling tendencies, a rapid rate of solution in water, and a desirable cloud point, are, in effect, conditions percedent to the beneficial utilization of a surfactant's basic functions.

Obviously, the worth of an alcohol-derived surfactant is heavily dependent on the characteristics of the alcohol. The basic character of the alcohol determines, to a large extent, whether the alcohol can be satisfactorily and conveniently converted to a surfactant material and whether the surfactant will successfully demonstrate the aforementioned attributes. In summary, the alcohol must be biodegradable and exist in a convenient form, such as in the liquid state at room temperature, in order to enable successful utilization in a wider variety of applications.

To these ends, and in view of recent ecology awareness, alcohols which are essentially linear in nature, such as those derived from natural sources, were necessarily desired by the detergent and related industries for their biodegradable nature. For many practical reasons, including costs, product control, and availability of such natural alcohol sources as fats, oils and waxes, manufacturers have turned to synthesizing alcohols, and their derivatives, which simulate the straight chain character of the naturally occurring products. U.S. Pat. No. 3,598,747 is representative of such an endeavor. Therein, Ziegler-type primary linear alcohols are prepared from trialkylaluminum mixtures made by way of ethylene polymerization, subsequent oxidation, and hydrolysis of the resultant aluminum alkoxides. U.S. Pat. No. 3,391,219 representatively describes the preparation of such trialkylaluminum mixtures and further exemplifies the desire to prepare a highly pure linear alpha-olefin, such as one suitable for subsequent alcohol preparation.

The high linearity of the Ziegler-type alcohols is reported to result in a high degree of biodegradability. The unsuitability and the avoidance of the branched-type alcohols, and their derivatives, in the surfactant area is additionally exemplified in U.S. Pat. Nos. 3,488,384; 3,504,041 and 3,567,784. Notably, a major application for the Ziegler-type alcohols has been in nonionic surfactant production.

Another method now customarily employed for producing similar alcohols is the process comprising reacting linear olefins with carbon monoxide and hydrogen under oxo reaction conditions. Heretofore, however, several companies were employing propylene tetramer feedstocks in the named oxo reaction to produce tridecylalcohol but the branched nature of the alcohol virtually eliminated it as a serious candidate in the surfactant area.

In the present conventional oxo processes, linear alpha-olefin feeds are used whereby a mixture of normal and 2-alkyl branched primary alcohols are produced. Because approximately 30 to 40 wt.%, and greater, of the alcohols have 2-alkyl branching, the conventional oxo alcohol method has been subjected to criticism. More recently, however, efforts in improving the oxo process have resulted in oxo alcohols having considerably less 2-alkyl branching. U.S. Pat. Nos. 3,239,569 and 3,239,571 illustrate such facts.

It has been reported, such as by the Stanford Research Institute, *Linear Higher Alcohols*, Report No. 27, Aug. 1967, at pages 3 and 133, that these more recent oxo alcohols having substantially less 2-alkyl branching are biodegradable because of the occurrence of branching at the favorable 2-position, which type of branching has only a relatively small detrimental effect on the biodegradability of its derivatives. It is evident, therefore, from the above-stated art that branched alcohols for surfactant production are to be otherwise avoided.

Other alcohol types have also been produced by the oxidation of normal paraffins but, unlike those alcohols produced by the ethylene polymerization process and those generally derived from natural origins, are secondary alcohols. The secondary alcohols, unlike the corresponding primary alcohols, in some surfactant applications, such as in the sulfated alcohol area, do not demonstrate the same desired properties. The secondary alcohols have other reported disadvantages.

As will be hereinafter more fully presented, the known alcohols or their surfactant derivatives, lack in varying degrees some of the heretofore detailed criteria that govern the overall suitability and/or acceptability of the alcohol and/or its surfactant derivatives. Accordingly, the heretofore known alcohols do not generally exist in a convenient liquid state and, except for those alcohols below undecanol, and the highly branched alcohols, such as prepared from propylene and butylene trimers, tetramers, and the like, they can be generally characterized as solid or relatively solid materials at or near room temperature. The latter named branched alcohols are unsuitable for surfactant application because of their resistance to biodegradation.

It is clearly evident that there is a definite and acute need for higher molecular weight alcohols that are liquid at room temperature, biodegradable and able to meet the basic standards that regulate whether the useful attributes of the alcohol and its surfactant derivatives can be fully utilized.

SUMMARY OF THE INVENTION

Therefore, in accordance with our invention, novel vinylidene alcohols are provided which can representatively depicted by the formula

(I)

wherein individually, x and y are numbers from 1 to 15 and the sum of x and y is in the range of 6 to 16. Surprisingly, such alcohol compositions are not only biodegradable but exist at room temperature in the liquid state. Accordingly, our novel alcohol compositions, when compared to the biodegradable prior art alcohols, possess freezing point (melting point) values far below anything heretofore known. Our alcohol compositions, in addition to being easily facilitated in a variety of applications, have effectively broadened the molecular weight range of surfactant suitable alcohols.

Further, the novel biodegradable ethoxylated derivatives of our unusual alcohols possess distinguishingly unique characteristics. For instance, the ethoxylates of our alcohols are products having excellent detersive and surfactant activity over a broader molecular weight range of the alcohol. Comparison of our ethoxylated alcohols with other prior art biodegradable ethoxylates is accurately and representatively portrayed at similar cloud points, the cloud point being the temperature at which a one wt. % aqueous solution of the surfactant turns from clear to cloudy as the temperature of the solution is raised. The particular cloud point of the surfactant is very important and the surfactant must obviously meet the cloud point specifications of the practitioner if the surfactant is to be commercially acceptable. For most general applications, cloud point specifications are preferably between 55°C. and 65°C. Recognizably, some specialized applications require a somewhat higher cloud point.

The synthetic alcohol ethoxylate derivatives of this invention exhibit outstanding qualities within said specifications. Therefore, when a comparison is made of our synthetic alcohol ethoxylate compositions with the related alcohol derived products now in the art, our compositions demonstrate superior wetting ability and much faster rates of water solubility. Perhaps most exciting is the fact that our herein defined alcohol derived surfactant compositions have a reduced tendency to gel in water at room temperature, a condition that has plagued the ethoxylates of the Ziegler and oxo-type alcohols previously mentioned. A further surprising advantage is that certain of our alcohol ethoxylate compositions are synergistic in wetting ability.

DESCRIPTION OF THE PREFERRED EMBODIMENTS

It should be noted that our novel compositions have been herein referred to as vinylidene alcohols and vinylidene ethoxylates. The term "vinylidene" has been employed for convenience to describe our compositions because vinylidene olefins have herein been employed to provide these novel compositions. Accordingly, "vinylidene olefins" herein referred to are those corresponding to the following representative formula:

(II)

wherein R and R' are linear alkyl radicals having a total of 8 to 18 carbon atoms and wherein R and R' taken individually represent a $C_2$ to $C_{14}$ alkyl radical, preferably a $C_4$ to $C_{10}$ alkyl radical. Therefore, the term "vinylidene alcohol" as used throughout the specification and/or claims designates those alcohols represented by Formulas I, III and IV herein and, correspondingly, the term "vinylidene ethoxylate" is used herein to designate those ethoxylates represented by Formula V herein.

The vinylidene alcohols of this invention can be prepared by the hydroformylation of the vinylidene olefins whereby said vinylidene olefins are reacted with carbon monoxide and hydrogen to form the vinylidene alcohols of Formula I. It is also possible to produce the vinylidene alcohols of Formula I by reaction of the vinylidene olefins of Formula II to yield the unsaturated vinylidene alcohols of Formulas III and IV, which can thereafter be hydrogenated to the saturated vinylidene alcohols of Formula I:

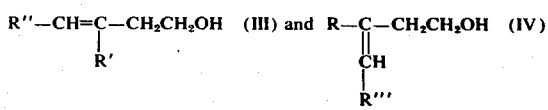

wherein, individually, R" and R'" are a linear alkyl radical containing at least one carbon atom and R and R', individually, are containing from about 2 to 14 carbon atoms and wherein the total carbon atoms of R" and R' in Formula III or R and R'" in Formula IV is in the range of 7 to 17. The vinylidene alcohols prepared by either the hydroformylation or formaldehyde addition reactions contain one more carbon atom than the olefin starting material.

For some unexplained reason, the vinylidene olefins used in our invention are unusually reactive with formaldehyde and formaldehyde-yielding components. Further, the formaldehyde addition process is so selective that when the vinylidene olefins of this invention are utilized in this process, the primary alcohol product contains 90 to 100 wt.%, usually 95 wt.% and greater, of the novel compositions represented by Formulas III and IV. These alcohols, being unsaturated, can be hydrogenated by conventional means to form vinylidene alcohols such as represented by Formula I. It will be apparent that upon hydrogenation of a mixture of vinylidene alcohol isomers described by Formulas III and IV, which are formed by the formaldehyde reaction with a vinylidene olefin, only one saturated vinylidene alcohol is produced.

Use of the stated hydroformylation process for preparing our novel compositions provides vinylidene alcohols represented by Formula I, along with smaller amounts of other isomers. There is a small proportion of the isomer of the vinylidene alcohol of Formula I with the branching in the 2- or alpha position. Also, there will be produced small proportions of other isomers with the branching in other positions due to some isomerization of the double bond which occurs during the hydroformylation process. However, when using the hydroformylation oxo process, from about 25 to about 90 wt.% of the vinylidene alcohols produced will be of the Formula I type.

Our novel compositions include, therefore, mixtures of vinylidene alcohols, or mixtures of the corresponding vinylidene ethoxylates, such as a mixture of those representatively depicted in Formulas II and IV or a mixture of compounds represented by Formula I and its isomers. As herein noted, the vinylidene alcohols will have one more carbon atom than did the vinylidene olefin from which they can be obtained. Accordingly, if a particular vinylidene olefin, such as a $C_{14}$, is employed in the hydroformylation or formaldehyde addition reaction, a $C_{15}$ alcohol which corresponds to one or more of the alcohols represented by Formulas I, III and IV are produced. In like manner, where mixtures of olefins, such as a mixture of $C_{14}$ and $C_{16}$ olefins, are employed, mixtures of $C_{15}$ and $C_{17}$ vinylidene alcohols are produced which correspond to one or more of the representative formulas.

Our inventive compositions, as herein depicted by representative formulations, include, therefore, mixtures of vinylidene alcohols or correspondingly vinylidene ethoxylates, such as a mixture of $C_{12}$ and $C_{13}$ alcohols as well as covering mixtures of alcohols, such as a mixture of $C_{14}$ vinylidene alcohols represented by the above formulas. The particular vinylidene alcohols represented by Formula I are generally preferred because they are very representative, or highly illustrative of, the many unusual and unexpected characteristics of our novel compositions.

The alcohols of this invention are employed to provide novel alcohol ethoxylates by conventional ethoxylation processes and can be representatively depicted as follows:

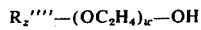   (V)

wherein $R''''$ is an alkyl radical which corresponds to the alkyl portion of the above-represented vinylidene alcohols, $w$ is a number of from 7 to 15 and preferably from 7 to 12. $R''''$, therefore, is an alkyl radical containing 11 to 21 carbon atoms and is selected from the following radicals:

a) 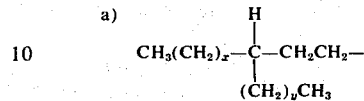

wherein, individually, $x$ and $y$ are integers from 1 to 15 and the sum of $x$ and $y$ is in the range of 6 to 16;

b) 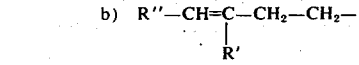

and c) 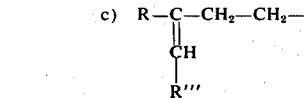

wherein R, R', R'' and R''' are as previously defined.

It is understood that when a plurality of ethylene oxide units are condensed with a vinylidene alcohol, or mixture of alcohols, that various oxyethylene chain lengths will result. Accordingly, as used herein, the value of $w$ is an average number indicating the average number of oxy-ethylene units present. In order to further characterize a particularly surprising aspect of our invention, we have included in the above-mentioned formula the subscript $z$, which represents a number corresponding to the number of the carbon atoms contained in the alkyl radical $R''''$ and $z$ is within the range of 11 to 15. For example, when $z$ is 15 and $w$ is 11, , the vinylidene ethoxylate represented is the 11- mol ethoxylate adduct of the vinylidene alcohol, pentadecanol.

In this regard, we have surprisingly found that if the value of the ratio of $w$ to $z$, in this formula, is within the range of 0.685 to 0.755, the vinylidene ethoxylates not only will demonstrate the preferred surfactant requisites discussed throughout the specification, but they will, unlike the primary alcohols of the Ziegler and oxo process of the prior art, possess the significant advantage of having the particular cloud points that satisfy the general specifications of the industry.

Another startling aspect is the discovery that when $z$ is 13 and $w$ is in the range of 9 to 10, i.e., the 9 to 10-mol ethoxylate of our $C_{13}$ vinylidene alcohol, the vinylidene ethoxylate demonstrates synergistic wetting ability with other alcohol ethoxylates and particularly enhances the activity of the stated prior art alcohol ethoxylates.

In accordance with our invention, the vinylidene olefin starting materials, i.e., those represented by Formula II, can be prepared by a conventional process such as by dimerizing alpha-olefins, e.g., Alkyl—$CH=CH_2$, mixtures thereof, and the like. For example, a mixture of $C_6$ to $C_{10}$ alpha-olefins can be used. A suitable process to produce vinylidene olefins is representatively described in U.S. Pat. No. 2,695,327. Typical vinylidene olefins are 2-hexyldecene-1, 2-octyldecene-1, 2-octyldodecene-1, and the like.

The alpha-olefins can be provided via the conventional conversion of ethylene by a combined growth-displacement reaction using Ziegler-type polymerization catalysts such as the trialkylaluminums. The resultant olefin fraction can be separated and the particular olefin fraction desired can be recovered for vinylidene olefin preparation such as by dimerization. Process conditions typical to a conventional oxo reaction can be employed. The conditions can be varied over broad ranges according to the desires of the practitioner and dictates of the particular catalyst used. Generally, temperatures in the range of about 25°C. to 250°C. and pressures in the range of about 15 to 10,000 psig can be employed. Conventional catalysts and conditions known to enhance alcohol production selectively over aldehydes can be employed. Catalysts such as those derived from cobalt and rhodium which are usually complexes of hydrogen, carbon monoxide, with or without other ligands, are also suitable. Catalyst complexes contining amines, phosphines, phosphites, pentavalent phosphorus, arsenic and antimony compounds, halides, carboxylate anions, and the like, are exemplary. Representative catalysts, conditions, and recovery techniques are exemplarily described in U.S. Pat. Nos. 3,594,425; 3,239,566; 3,239,571; 3,420,898 and in *Carbon Monoxide in Organic Synthesis*, Jurgen Falbe, Springer-Verlag, New York, 1970.

As previously stated, the formaldehyde addition process can also be employed. This process provides high selectivity and unexpectedly rapid and complete conversions of vinylidene olefins to our vinylidene alcohols. This process can be employed without a catalyst when temperatures are sufficiently high such as around 200°C. Acidic catalysts can be employed, if desired. Catalysts are preferred if temperatures less than 200°C. are employed to give better reaction rates. Exemplary catalysts suitable are $BF_3$ and complexes thereof, acetic acid, tin halides, such as stannic chloride, and the like. Temperatures up to that where decomposition begins can be employed. Generally, temperatures in the range of about 50°C. to 300°C. are used. Generally, pressures sufficient to maintain an essentially liquid phase are used. Exemplary conditions, and the like, are further described in U.S. Pat. Nos. 2,335,027; 2,624,766 and in *Angewandte Chemie, International Edition*, H. M. R. Hoffmann, 8, 556 (1969).

The vinylidene alcohols of this invention can be converted to our vinylidene ethoxylates by way of typical alkoxylation procedures, such as wherein an alcohol and ethylene oxide are condensed in the presence of alkaline catalysts, such as alkali metal hydroxides, alkali metal alcoholates or phenolates or metallic sodium and potassium, and the like. Sodium and potassium hydroxide are exemplary catalysts.

Other methods for preparing the alkyl polyoxyethylene adducts of our alcohols can be employed such as by the conversion of the alcohol to the corresponding alkyl halide, e.g., alkyl bromide, by means of $PBr_3$, followed by reaction with the appropriate glycol, i.e.,

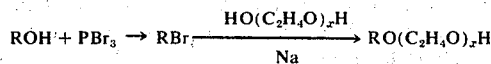

Another method is by the stepwise reaction of the alcohol with ethylene chlorohydrin.

The base catalyzed addition of ethylene oxide to the alcohol is the preferred method and it readily enables the control of the number of oxyethylene units added to the alcohol. Usually in this process, temperatures in the range of about 100°C. to 350°C. are employed. Generally, pressures sufficient to maintain an essentially liquid phase are used. One representative process is described in U.S. Pat. No. 3,436,426. It should be noted that the ethoxylates of this invention have an advantage over the secondary alcohol ethoxylates, previously mentioned, in that they can be easily prepared in a one-step ethoxylation process.

The foregoing discussion and description is further illustrated by the following examples which depict various of our vinylidene alcohol and alcohol ethoxylate compositions and demonstrate many of the distinguishing aspects of this invention. The examples are not to be interpreted as a limitation on the scope of the foregoing discussion and description or on the materials therein employed. The compositions prepared in the following examples were verified by nuclear magnetic resonance, infrared, chromatographic and hydroxyl number analysis.

EXAMPLE I

This example, as well as Examples II through V, demonstrate preparation of our novel primary alcohol compositions such as those corresponding to Formulas III and IV hereinabove.

To a one-gallon autoclave was charged 2,060 grams of a $C_{10}$ vinylidene olefin fraction comprising a 50:50 weight mixture of 2-ethyl-1-octene and 2-butyl-1-hexene and 230 grams of paraformaldehyde. The autoclave was flushed with nitrogen and heated at 250°C. for one hour. The reactor effluent was washed twice with water and distilled to provide 690 grams of vinylidene $C_{11}$ alcohols, b.p. 119° to 127°C. at 20 mm. Referring to Formulas III and IV, about 50 wt.% of the product comprised a composition wherein R" is propyl and R' is butyl. About 50% of the product comprised a mixture of (a) wherein R" is pentyl and R' is ethyl and (b) wherein R is methyl and R''' is hexyl. Accordingly, almost 100 wt.% of the products comprised a mixture of 3-ethyl-non-3-enol, 3-hexyl-pent-3-enol, and 3-butylhept-3-enol.

EXAMPLE II

A one-liter stirred autoclave was charged with 340 grams of a $C_{12}$ vinylidene olefin fraction comprising 2-butyl-1-octene and 32 grams paraformaldehyde. The reactor was flushed with nitrogen and heated at 275°C. for one hour. The effluent was washed with successive 200 ml. portions of an aqueous solution of 0.5 wt.% sulfuric acid and 5 wt.% sodium bicarbonate. The washed effluent was dried over anhydrous sodium sulfate, filtered, and distilled to give 95 grams of product, b.p. 105°C. to 110°C. at 3 mm. Over 90 wt.% of the product was identified as 3-butylnon-3-enol, 3-hexyl-hept-3-enol and their formate esters.

EXAMPLE III

A one-gallon stirred autoclave was charged with 1,960 grams of a $C_{14}$ vinylidene olefin fraction comprising a 50:50 weight mixture of 2-butyl-1-decene and 2-hexyl-1-octene and 100 grams paraformaldehyde. The autoclave was flushed with nitrogen and heated at 250°C. for one hour. The effluent was washed with water and distilled to give 1434 grams unreacted $C_{14}$ olefins and 421 grams $C_{15}$ alcohols, b.p. 135° to 140°C. at 5 mm. The products were about 95 wt.% of a 50:50 mixture of 3-hexylnon-3-enol and a mixture of 3-butylundec-3-enol and 3-octylhept-3-enol.

EXAMPLE IV

A one-liter stirred autoclave was charged with 450 grams of a $C_{16}$ vinylidene olefin fraction comprising 2-hexyl-1-decene and 33 grams of paraformaldehyde. The autoclave was flushed ith nitrogen and heated at 250°C. to 252°C. for one hour. The effluent was washed once with 200 ml. water and distilled to give 356 grams unreacted olefin and 90 grams of product, b.p. 150°C. to 157°C. at 5 mm. The product fraction was identified as over 95 wt.% of a mixture of 3-hexylundec-3-enol and 3-octylnon-3-enol.

EXAMPLE V

A three-gallon autoclave was charged with 6,048 grams of a $C_{18}$ vinylidene olefin fraction comprising a 50:50 wt.% mixture of 2-octyl-1-decene and 2-hexyl-1-dodecene and 396 grams of paraformaldehyde. The autoclave was flushed with nitrogen and heated at 250°C. to 254°C. for 1.5 hours. The temperature was reduced to 200°C. and 400 ml. water was injected into the autoclave. The temperature was maintained at 185°C. to 190°C. for one hour. The reactor effluent was washed twice with water and distilled to give 1,585 grams $C_{19}$ alcohols, b.p. 153°C. to 159°C. at 0.5–0.7 mm. The product alcohol comprised about 50 wt.% of 3-decylnon-3-enol and about 50 wt.% of a mixture of 3-octylundec-3-enol and 3-hexyltridec-3-enol.

EXAMPLE VI

This example, as well as Examples VII through X, demonstrate the hydrogenation of unsaturated vinylidene alcohols to provide saturated alcohols corresponding predominately to the alcohols of Formula I. The unsaturated $C_{11}$ vinylidene alcohols produced in Example I, above, were hydrogenated over a nickel-copper-chromium hydrogenation catalyst at 154°C. to 165°C. and 700 to 1,800 psig. Distillation of the filtered effluent gave 353 grams of a saturated $C_{11}$ alcohol, b.p. 114°C. to 116°C. at 10 mm. The primary alcohol product was essentially a 100 wt.% mixture of 3-ethylnonanol and 3-butylheptanol.

EXAMPLE VII

A 400-ml. sample of $C_{13}$ unsaturated vinylidene alcohols prepared as in Example II was hydrogenated over a reduced nickel catalyst at 158°C. to 163°C. at 1,175 to 2,100 psig. The reactor effluent was filtered and a portion of it distilled to give 311 grams of $C_{13}$ saturated vinylidene alcohols, b.p. 135°C. to 138°C. at 8 mm. The vinylidene alcohol was essentially 100 wt.% 3-butylnonanol.

EXAMPLE VIII

A 1,300-gram sample of unsaturated $C_{15}$ vinylidene alcohol, prepared as in Example III, was hydrogenated over a nickel-copper-chromium hydrogenation catalyst at 138°C. to 164°C. at 650 to 1,050 psig. The hydrogenation material was distilled to give 1,240 grams of $C_{15}$ vinylidene alcohols, b.p. 117°C. to 121°C. at 0.35 to 0.60 mm. The saturated vinylidene alcohols were a mixture of 3-butylundecanol and 3-hexylnonanol.

EXAMPLE IX

A 920-gram sample of unsaturated $C_{17}$ vinylidene alcohol, prepared as in Example IV, was hydrogenated over a nickel-copper-chromium hydrogenation catalyst at 163°C. to 173°C. at 550 to 1,100 psig. The hydrogenation effluent was filtered and distilled to give 804 grams of $C_{17}$ saturated vinylidene alcohols, b.p. 155°C. to 157°C. at 3.0 mm. The vinylidene alcohol product contained greater than 90 wt.% 3—hexylundecanol.

EXAMPLE X

A 1,000-gram sample of $C_{19}$ unsaturated vinylidene alcohol that was prepared in previous Example V was hydrogenated over a nickel-copper-chromium hydrogenation catalyst at 153°C. to 165°C. at 725 to 1,100 psig. The hydrogenated material was distilled to give 839 grams of $C_{19}$ saturated vinylidene alcohols, b.p. 156°C. to 161°C. at 0.7 mm. The vinylidene alcohol product was over 95 wt.% of a mixture of 3-hexyltridecanol and 3-octylundecanol.

EXAMPLE XI

This example, as well as Examples XII through XVI, demonstrates the preparation of our vinylidene alcohols by way of the hydroformylation process. The vinylidene alcohol compositions produced corresponded to the above Formula I.

A 1,400-ml. rocking autoclave was charged with 500 grams of $C_{10}$ vinylidene olefin fraction comprising a 50:50 wt.% mixture of 2-ethyl-1-octene and 2-butyl-1-hexene, 17 grams of a cobalt octoate solution (12 wt.% cobalt), and 14 grams of tributylphosphine. The reaction mixture was contacted with a 1:1 mixture of hydrogen and carbon monoxide at 180°C. to 187°C. and 1,500 to 3,000 psig for four hours. The reactor effluent was distilled to give 219 grams of a mixture of $C_{11}$ aldehyde and $C_{11}$ vinylidene alcohol, b.p. 105°C. to 125°C. at 15 mm. A portion of the mixture, i.e., the $C_{11}$ oxo product, was hydrogenated over a reduced cobalt catalyst at 160°C. at 1,000 to 1,300 psig for one hour. The reaction mixture was filtered and distilled to provide 156 grams of $C_{11}$ primary vinylidene alcohol, b.p. of 112°–117°C. at 10 mm.

EXAMPLE XII

A 1,400-ml. rocking autoclave was charged with 400 grams of a $C_{12}$ vinylidene olefin comprising 2butyl-1-octene, 7 grams of a solution of cobalt linoresinate (6 wt.% cobalt) and 10 grams of tris(nonylphenyl)phosphate. The autoclave was flushed with synthesis gas (1:1 weight mixture of hydrogen and carbon monoxide) and heated to 160°C. Synthesis gas was introduced at a constant pressure of 3,000 psig and the temperature held at 160°C. for one hour. The reactor effluent was flashed in a wiped film evaporator at 220°C. and 1.5 mm. pressure to give 401 grams overhead material and 53 grams bottoms.

The overhead fraction was hydrogenated over a reduced cobalt catalyst at 180°C. at 400–1,000 psig hydrogen pressure. Distillation of 340 grams of the hydrogenated material provided 242 grams of $C_{13}$ vinylidene primary alcohols, b.p. 120°C. to 130°C. at 5 mm. About 53 wt.% of the vinylidene alcohols conformed to Formula I, e.g., 3-butyl-1-nonanol, and the remainder was a mixture of isomers of the $C_{13}$ vinylidene with branching at other locations.

EXAMPLE XIII

A mixture of 50 wt.% 2-butyl-1-octene, 25 wt.% 2-butyl-1-decene and 25 wt.% 2-hexyl-1-octene containing 0.1 wt.% cobalt (as cobalt linoresinate) and 1.5 mols tris(nonylphenyl)phosphate per gram atom of cabalt was fed to a continuous tubular reactor with an excess of 1:1 mixture of hydrogen and carbon monoxide. The reaction was conducted at a liquid hourly space velocity of 1 gram/hour/ml. The reactor effluent was passed through a wiped film evaporator to separate the unreacted olefins and product aldehydes and alcohols as overhead material from the catalyst.

The flashed material was hydrogenated in a continuous fixed bed reactor over a reduced cobalt catalyst at 1,500 psig, and 165°–190°C. temperature and at a liquid hourly space velocity of 1 gram/hour/ml. Distillation of the hydrogenation reactor effluent provided $C_{13}$ primary vinylidene alcohols, b.p. 125°C. at 5 mm. and $C_{15}$ primary vinylidene alcohols, b.p. 150°C. to 157°C. at 5 mm. The $C_{13}$ alcohols were essentially identical to those produced in Example XII. The product boiling at 150°–157°C. was a mixture of isomers of $C_{15}$ primary vinylidene alcohols with the predominant isomer being as shown in Formula I as demonstrated by chromatographic, spectral and wet analysis methods.

EXAMPLE XIV

A 1,400-ml. rocking autoclave was charged with 500 grams of $C_{16}$ vinylidene olefin comprising 2-hexyl-1-decene and 75 grams of a heptane solution of cobalt octacarbonyl containing 3.6 grams cobalt. This mixture was treated with synthesis gas, as in the previous examples, at 130°–133°C. and 2,000–3,000 psig for 2.5 hours. The reactor effluent was decobalted by stirring with 300 ml. of an aqueous solution containing 7 wt.% acetic acid and 3 wt.% sodium acetate for one hour at 60°–65°C. The mixture was cooled and the aqueous layer separated to give 596 grams material. The recovered material was hydrogenated over a cobalt catalyst at 160°–190°C. and 200–2,000 psig for 75 minutes. The catalyst was removed by filtration and the product distilled to provide 349 grams of $C_{17}$ primary vinylidene alcohol, b.p. 150°–170°C. at 3–4 mm.

EXAMPLE XV

A 1,400-ml. rocking autoclave was charged with 530 grams of a 50:50 weight mixture of a $C_{18}$ vinylidene olefin fraction comprising 2-hexyl-1-dodecene and 2-octyl-1-decene, and 12 grams of a rhodium heptanoate solution containing 3 wt. % rhodium. This solution was treated with a 1:1 mixture of hydrogen and carbon monoxide at 124°–130°C. and 750–3,000 psig for two hours. The autoclave was cooled and vented and 50 grams of a reduced cobalt hydrogenation catalyst was added. The reaction mixture was treated with hydrogen at 160°C. and 975–1,300 psig for 3.25 hours. The reactor effluent was filtered and distilled to provide 442 grams of $C_{19}$ primary vinylidene alcohols, b.p. 153°C. to 158°C. at 1 mm.

EXAMPLE XVI

A 1,400-ml. rocking autoclave was charged with 500 grams of a $C_{20}$ vinylidene olefin comprising 2-octyl-1-dodecene and 75 grams of cobalt octacarbonyl solution in heptane containing 3.6 grams of cobalt. This mixture was contacted with synthesis gas as in the previous examples at 130°–140°C. and 1,200–3,000 psig for three hours. The autoclave was cooled and vented and 40 grams of a reduced cobalt hydrogenation catalyst was added. This mixture was treated with hydrogen at 170°C. and 1,375–2,000 psig for 1.5 hours. The reactor effluent was filtered and distilled to give 224 grams of $C_{21}$ primary vinylidene alcohol, b.p. 168°C. to 172°C. at 0.3–0.5 mm.

EXAMPLE XVII

In a stainless steel autoclave was placed 100 grams of $C_{13}$ primary vinylidene alcohol prepared as in Example XIII. The olefin feed for the vinylidene alcohol preparation was made using a vinylidene olefin product prepared from hexene-1 dimerization. Flaked potassium hydroxide (0.5 gram) was added, and the contents of the autoclave were heated to 140°C. Ethylene oxide was added at such a rate that the pressure was maintained at about 50 psig and the temperature at about 140°C. When 220 grams of ethylene oxide had been added, the catalyst was neutralized with 0.54 grams of oxalic acid. Filter aid was added and the product filtered to provide a vinylidene alcohol ethoxylate having a cloud point of 62°C. and a pour point of 16°C. A small amount of this product was poured into water at approximately 25°C. and the vinylidene alcohol ethoxylate dissolved readily without forming a gel. Contrarily, an ethoxylate made from a $C_{13}$ alcohol prepared by the hydroformylation of dodecene-1 gelled immediately when added to water and was dissolved only with great difficulty.

EXAMPLE XVIII

The novel vinylidene alcohols of this invention are herein further compared with corresponding prior art alcohols. Type A primary vinylidene alcohols represent those vinylidene alcohols prepared according to Examples I through V. Type B primary vinylidene alcohols represent those vinylidene alcohols prepared according to Examples VI through X. Type C primary vinylidene alcohols represent those prepared by Examples XI through XVI. Type D prior art primary alcohols are those oxo alcohols made from the hydroformylation of linear alpha-olefins. Type E prior art primary alcohols represent those normal primary alcohols prepared from trialkylaluminum.

Certain novel and unique characteristics of our primary vinylidene alcohols are demonstrated by the following data reported in Table 1. It is evident that with the sole exception of the $C_{21}$ vinylidene alcohol prepared by the hydroformylation of 2-octyl-1-dodecene, our vinylidene alcohols do not freeze above $-50°C$. It is particularly noteworthy and surprising that our vinylidene alcohols exhibit significantly lower freezing points than the prior art alcohols that contain 2-monoalkyl branching.

TABLE 1

MELTING POINTS (FREEZING POINTS)°C
ALCOHOL TYPE

| Run No. | Carbon No. | (A) Unsaturated Vinylidene Alcohol | (B) Saturated Vinylidene Alcohol | (C) Oxo Vinylidene Alcohol | (D) Prior Art Oxo Alcohol | (E) Prior Art Normal Primary Alcohol |
|---|---|---|---|---|---|---|
| 1 | 11 | <−30° | <−50° | <−50° | −4−3°[1] | 19° |
| 2 | 12 | | | | 14−20°[2] | 24.8° |
| 3 | 13 | <−50° | <−50° | <−50° | 17−21°[3] | 30.5° |

TABLE 1-continued

MELTING POINTS (FREEZING POINTS)°C
ALCOHOL TYPE

| Run No. | Carbon No. | (A) Unsaturated Vinylidene Alcohol | (B) Saturated Vinylidene Alcohol | (C) Oxo Vinylidene Alcohol | (D) Prior Art Oxo Alcohol | (E) Prior Art Normal Primary Alcohol |
|---|---|---|---|---|---|---|
| 4 | 14 | | | | | 39–40° |
| 5 | 15 | <−50° | <−50° | <−50° | 25–27°[4] | 43.8° |
| 6 | 16 | | | | | 50° |
| 7 | 17 | <−50° | <−50° | <−50° | 42–45°[5] | 54° |
| 8 | 18 | | | | | 58.5° |
| 9 | 19 | <−50° | <−50° | <−50° | | 62–63° |
| 10 | 20 | | | | | 65.5° |
| 11 | 21 | | | 21° | | |

[1] In addition to normal alcohol product contained 35 wt. % 2-alkyl branching.
[2] A mixture (40:60) $C_{12}$–$C_{13}$ oxo alcohol (MFCDOL® 23) contains 2-methyl branching.
[3] See Footnote (1), 40% 2-monoalkyl branching.
[4] See Footnote (1), 42% 2-monoalkyl branching.
[5] See Footnote (1), 45% 2-monoalkyl branching.

EXAMPLE XIX

The novel vinylidene alcohols of this invention are herein compared to the prior art liquid primary alcohols, e.g., tridecyl alcohol prepared by the hydroformylation of propylene tetramer. Contrary to expectations from the known teachings, the data reported in Table 2 clearly demonstrate the biodegradability of our vinylidene alcohols.

The tests were run in a Hach Manometric BOD apparatus, Model 2173. Each test used 100 mg of the subject alcohol and 157 ml of BOD dilution water containing 10% or 20% by volume of bacterial seed. The bacterial seed was either raw domestic sewage from a sewage treatment plant which had been settled for 24 hours at 20°C and filtered through glass wool or an acclimated seed. The acclimated bacterial seed was obtained by acrating raw sewage with daily settling and siphoning off of two-thirds of the liquid and feeding increasing increments of test alcohols along with fresh sewage for a one-week period.

The ethylene oxide adducts have been characterized by their cloud point of a one wt. % aqueous solution. The novel vinylidene alcohol ethoxylates of this invention are herein compared with corresponding prior art alcohol ethoxylates. As previously demonstrated in Example XVII, most of the prior art primary alcohol ethoxylates which are generally employed for surfactant application undergo gel formation when the nonionic ethoxylate is added to water. Accordingly, aqueous solutions are prepared often with great difficulty. As previously stated the vinylidene alcohol ethoxylates of this invention show a significantly less tendency to form such gels. This example, therefore, demonstrates the comparative rapidity at which our vinylidene alcohol ethoxylates are dissolved in water at 25°C. Obviously, the rate of solution in water at room temperature is important for many utilizations of the alcohol ethoxylates. This characteristic further permits convenient room temperature mixing, reacting, and the like.

This example was conducted by placing 60 ml of deionized water at 25°C in a 150 ml beaker in which a

TABLE 2

FIVE-DAY BIO-CHEMICAL OXYGEN DEMAND (PER 100 mg OF SAMPLE)[a]

| Run No. | Alcohol Type | Carbon No. | Raw Sewage Seed 10% | Raw Sewage Seed 20% | Acclimated Seed 10% | Acclimated Seed 20% |
|---|---|---|---|---|---|---|
| 1 | C[b] | 13 | 59 ppm | 58 ppm | 126 ppm | |
| 2 | A[c] | 13 | | | | 118 ppm |
| 3 | B[d] | 15 | | | | 92 ppm |
| 4 | A | 17 | | | | 92 ppm |
| 5 | Tridecyl | 13 | 0 | 0 | 81 ppm | 79 ppm |

[a] Standard Methods for the Examination of Water and Wastewater, 12th Edition, 1965, p. 417, American Public Health Association, New York, N.Y.
[b] Oxo vinylidene alcohol, same as reported in Table 1.
[c] Unsaturated vinylidene alcohol, same as reported in Table 1.
[d] Saturated vinylidene alcohol, same as reported in Table 1.

EXAMPLE XX

Using the procedure of Example XVII, many different carbon numbered alcohols from $C_{11}$ to $C_{21}$ were converted to ethylene oxide adducts. The alcohols were made from the vinylidene olefins either by the oxo reaction or by the formaldehyde addition process. The vinylidene alcohols from the formaldehyde reaction were employed both as the unsaturated alcohol or as the hydrogenated (saturated) alcohol where indicated.

magnetic stirrer was employed. Ten drops of the liquid alcohol ethoxylate to be tested was rapidly added to the water while stirring the solution at a constant rate by means of the magnetic stirrer. An electric timer, triggered when the first drop was added, measured the elapsed time for complete dissolution of the added surfactant. Three duplicate runs were made for each sample tested and the average elapsed time was calculated. These average times in seconds for the various alcohol ethoxylates are reported in Table 3.

TABLE 3

| Run No. | Alcohol Type[a] | Carbon No. Alcohol | Cloud Point, °C. Alcohol Ethoxylate | Solution Time Seconds |
|---|---|---|---|---|
| 1 | D | 13 | 62 | 206 |
| 2 | C | 13 | 49 | 30 |

TABLE 3-continued

| Run No. | Alcohol Type[a] | Carbon No. Alcohol | Cloud Point, °C. Alcohol Ethoxylate | Solution Time Seconds |
|---|---|---|---|---|
| 3 | C | 13 | 70 | <10 |
| 4 | A | 13 | 56 | <10 |
| 5 | B | 13 | 44 | 14 |
| 6 | Tridecyl | 13 | 39.5 | 30 |
| 7 | D | 15 | 53.5 | 400 |
| 8 | C | 15 | 64 | 126 |
| 9 | B | 15 | 55 | 23 |
| 10 | B | 15 | 76 | 190 |
| 11 | D | 17 | 52 | >400 |
| 12 | B | 17 | 51.3 | 60 |
| 13 | D | 11/13[b] | 60 | 101 |
| 14 | C | 11/13[b] | 61 | 70 |
| 15 | D | 13/15[c] | 59 | 292 |
| 16 | C | 13/15[d] | 50 | 28 |
| 17 | C | 13/15[d] | 65 | 20 |
| 18 | C | 13/15[d] | 88 | 131 |
| 19 | D | 11/13/15[e] | 61 | 198 |
| 20 | D/C/C[f] | 11/13/15[f] | 63 | <10 |
| 21 | D/D/C/C[g] | 11/13/13/15[g] | 49 | 19 |
| 22 | D | 12-15[h] | 50 | 343 |
| 23 | D | 12-15[i] | 90 | 175 |
| 24 | D | 12-13[j] | 45 | 171 |
| 25 | E | 12-18[k] | 59 | 298 |
| 26 | E | 12-14[l] | 55 | 263 |
| 27 | E | 12[m] | 62 | >400 |

[a]The alcohol composition is the same as that reported in Table 1.
[b]25:75 wt. % mixture
[c]60:40 wt. % mixture
[d]57:43 wt. % mixture
[e]25:50:25 wt. % mixture
[f]40:40:20 wt. % mixture of type E/C/C alcohol as reported in Table 1.
[g]35:30:20:15 wt. % mixture of Type E/E/C/C/ alcohols as reported in Table 1.
[h]20:30:30:20 wt. % mixture of $C_{12}$, $C_{13}$, $C_{14}$, $C_{15}$ oxo alcohols, e.g., NEODOL 25 (7-mol ethylene oxide adduct). See footnote (2) Table 1.
[i]Same as (h) except 12 mol ethylene oxide adduct.
[j]6.5 Ethylene oxide adduct of NEODOL 23 alcohol (40:60 wt. % $C_{12}$—$C_{13}$).
[k]Ethylene oxide adduct of ALFOL 1218 alcohol (40:30:20:10 wt. % $C_{12}$, $C_{14}$, $C_{16}$, $C_{18}$).
[l]Ethylene oxide adduct of ALFOL 1214 alcohol (55:45 wt. % $C_{12}$—$C_{14}$).
[m]Ethylene oxide adduct of ALFOL 12 alcohol.

It is evident from the data reported in Table 3 that the vinylidene ethoxylates of this invention, e.g., from alcohols of Type A, B and C, are vastly superior to the linear alcohol ethoxylates prepared from either Ziegler alcohols, e.g., Type E alcohols, or from alcohols prepared by the hydroformylation of alpha-olefins, e.g., Type D alcohols. The advantage of incorporating the vinylidene ethoxylates of this invention with prior art products is demonstrated in Runs 20 and 21. Comparison of Runs 3, 8 and 17 demonstrate that when the $C_{13}$ vinylidene ethoxylate is incorporated with other vinylidene ethoxylates that the time to solution in seconds is much faster than would be predicted from the solution time in seconds of the individual components alone. The synergistic effects of the $C_{13}$ vinylidene alcohol ethoxylates of this invention will be further demonstrated herein.

EXAMPLE XXI

The novel vinylidene alcohol ethoxylates of this invention are herein compared with corresponding prior art alcohols as to wetting times. The alcohol types are the same as reported in Example XVIII and Table 1. Wetting times are measured by the Draves method (American Association for Textile Chemists and Colorists), Method No. 17–1952, at 25°C. The cloud point of the alcohol ethoxylates and the wetting time in seconds are reported in Table 4. The wetting times reported are for a 1.5 gm hook at 0.10 wt. % concentration. The following data demonstratively show the clear superiority of the vinylidene alcohol ethoxylates of this invention over the linear primary alcohol ethoxylates of the prior art in wetting performance. The data also effectively demonstrates the surprising superiority of the products of this invention over presently available commercial primary alcohol ethoxylates.

TABLE 4

| Run No. | Alcohol Type | Carbon No. Alcohol | Cloud Point, °C Alcohol Ethoxylate | Wetting Time, Seconds |
|---|---|---|---|---|
| 1 | D | 11 | 60 | 8.0 |
| 2 | C | 11 | 60 | 7.5 |
| 3 | B | 11 | 58.4 | 6.8 |
| 4 | D | 13 | 61 | 10.0 |
| 5 | A | 13 | 56 | 4.8 |
| 6 | B | 13 | 44 | 5.0 |
| 7 | C | 13 | 49 | 6.0 |
| 8 | D | 15 | 53.5 | 26 |
| 9 | A | 15 | 61 | 8.0 |
| 10 | B | 15 | 55 | 9.0 |
| 11 | C | 15 | 64 | 10.0 |
| 12 | D | 17 | 52 | 70 |
| 13 | A | 17 | 56 | 13 |
| 14 | B | 17 | 52 | 20 |
| 15 | C | 17 | 51.3 | 30 |
| 16 | C | 19 | 55 | 78 |

TABLE 4-continued

| Run No. | Alcohol Type | Carbon No. Alcohol | Cloud Point, °C Alcohol Ethoxylate | Wetting Time, Seconds |
|---|---|---|---|---|
| 17 | D | 11/13[a] | 57 | 10.5 |
| 18 | D | 13/15[b] | 57.5 | 17.0 |
| 19 | C | 13/15[c] | 65 | 9.8 |
| 20 | D | 11/13/15[d] | 59 | 14.0 |
| 21 | D/C/C[e] | 11/13/15[e] | 63 | 8.8 |
| 22 | D/D/C/C[f] | 11/13/13/15[f] | 49 | 8.0 |
| 23 | D[g] | 12/13 | 45 | 7.8 |
| 24 | D[h] | 12–15 | 71 | 21.8 |
| 25 | E[i] | 12–18 | 59 | 26.7 |
| 26 | Secondary Alcohol[j] | 60 | | 8.3 |

[a] 50:50 wt. % mixture
[b] 65:35 wt. % mixture
[c] 57:43 wt. % mixture
[d] 25:50:25 wt. % mixture
[e] 40:40:20 wt. % mixture
[f] 35:30:20:15 wt. % mixture
[g] Alcohol same as reported footnote [g], Table 3.
[h] 9 mol ethylene oxide adduct of alcohol reported in footnote [h], Table 3.
[i] Alcohol same as reported footnote [k], Table 3.
[j] TERGITOL 15-8-9.

EXAMPLE XXII clearly evident from the following data reported in Table 5.

TABLE 5

| Run No. | Alcohol Type | Carbon No. Alcohol | Cloud Point | CPS at 25°C. Wt. % Concentration | | | | | | | |
|---|---|---|---|---|---|---|---|---|---|---|---|
| | | | | 20 | 30 | 40 | 50 | 60 | 70 | 80 | 90 |
| 1 | D | 11 | 52 | 25 | 95 | 165 | 155 | 130 | 110 | 95 | 75 |
| 2 | D | 11 | 61.4 | 50 | 125 | 275 | 275 | 250 | 200 | 175 | 150 |
| 3 | D | 11 | 76 | 20 | 35 | 180 | gel[a] | >300 | 150 | 115 | 100 |
| 4 | C | 11 | 57 | 20 | 65 | 125 | 130 | 110 | 95 | 95 | 75 |
| 5 | C | 11 | 75.6 | 15 | 17 | 90 | 150 | 130 | 105 | 92 | 90 |
| 6 | C | 11 | 88 | 15 | 25 | 115 | gel[b] | 220 | 150 | 115 | 100 |
| 7 | D | 13 | 52 | 100 | 700 | gel[c] | 675 | 3,100 | 4,450 | 3,700 | 150 |
| 8 | D | 13 | 59 | 175 | 375 | gel[d] | | 600 | 1,400 | 1,200 | 175 |
| 9 | D | 13 | 69 | 75 | 175 | gel[e] | | | 3,300 | 1,800 | 200 |
| 10 | C | 13 | 48 | 50 | 400 | 350 | 300 | 3,300 | 5,000 | 3,500 | 150 |
| 11 | C | 13 | 53 | 100 | 300 | 400 | 500 | 4,100 | 6,790 | 250 | 150 |
| 12 | C | 13 | 64 | 75 | 200 | 650 | 550 | 450 | 2,450 | 200 | 140 |
| 13 | D/C[f] | 13 | 57 | 100 | 300 | 2,100 | 2,000 | 500 | 3,500 | 250 | 175 |
| 14 | D/C[g] | 13 | 59 | 50 | 200 | 6,000 | 400 | 400 | 2,200 | 200 | 150 |
| 15 | D/C[h] | 13 | 61.2 | 100 | 200 | 1,100 | 800 | 350 | 2,100 | 225 | 150 |
| 16 | D | 15 | 52.5 | 250 | 5,800 | 4,200 | 4,150 | 1,575 | 3,200 | 5,500 | 175 |
| 17 | D | 15 | 63.5 | 100 | 1,200 | gel[i] | | 42,000 | 7,500 | 7,500 | >7,500 |
| 18 | D | 15 | 72.5 | 100 | 150 | gel[j] | | | 5,000 | 2,400 | 200 |
| 19 | C | 15 | 51 | 150 | 750 | 900 | 550 | 2,000 | 2,800 | 3,450 | 200 |
| 20 | C | 15 | 64 | 125 | 750 | gel[k] | 28,000 | 5,800 | 8,250 | 6,700 | 100 |
| | D | 11/15[l] | 60.7 | 100 | 300 | gel[m] | | 1,000 | 5,000 | 4,400 | 200 |
| | D | 11/15[n] | 61.6 | 100 | 175 | 4,400 | 12,800 | 475 | 2,650 | 200 | 175 |
| | D | 11/15[o] | 62.0 | 75 | 150 | 2,400 | gel[p] | 2,500 | 400 | 250 | 3,250 |
| | D/C[q] | 11/15[q] | 60.5 | 50 | 400 | 1,450 | 1,300 | 4,100 | 6,880 | 5,560 | 5,600 |
| | C | 13/15[r] | 58.9 | 75 | 350 | 950 | 500 | 300 | 13,800 | 300 | 200 |
| | C | 13/15[s] | 60.0 | 50 | 500 | 15,500 | 1,650 | 3,000 | 5,100 | 5,300 | 200 |
| | D/D/C/C[t] | 11/13/13/15[t] | 49 | 100 | 200 | 300 | 250 | 175 | 1,850 | 200 | 200 |
| | C | 17 | 54 | 3,500 | 3,000 | 4,500 | 1,200 | 4,000 | 17,000 | 19,000 | 400 |

[a] gelled in 47–53% range.
[b] gelled in 49–53% range.
[c] gelled in 37–43% range.
[d] gelled in 35–52% range.
[e] gelled in 39–60% range.
[f] 80:20 wt. % mixture.
[g] 20:80 wt. % mixture.
[h] 50:50 wt. % mixture.
[i] gelled material in 36–52% range.
[j] gelled in 38–60% range.
[k] gelled in 37–42% range.
[l] 25:75 wt. % mixture.
[m] gelled in 35–55 range.
[n] 50:50 wt. % mixture.
[o] 75:25 wt. % mixture.
[p] gelled in 45–52% range.
[q] 20:30 wt. % mixture.
[r] 50:50 wt. % mixture.
[s] 20:30 wt. % mixture.
[t] 35:30:20:15 wt. % mixture.

To further exemplify the nongelling tendencies of the vinylidene alcohol ethoxylates of this invention, the following runs are presented. The type of alcohol employed to prepare the various ethoxylates reported in Table 5 are the same as those previously reported in Example XVIII and Table 1. The indicated alcohol ethoxylates were admixed with water in the reported concentrations. The viscosity of the aqueous mixture was measured in centipoises on a Brookfield viscometer at 25°C. The generally lower viscosities and the significant tendency of our compositions not to gel are

EXAMPLE XXIII

The instant example demonstrates another significant aspect of our invention and further exemplifies the vast differences between our novel alcohol ethoxylates from those of the prior art.

As heretofore discussed, preferred vinylidene alcohol ethoxylates conform to the following formula:

wherein the ratio of w/z is in the range of 0.685 to 0.755 and w and z are as previously defined. Accordingly, vinylidene ethoxylate compositions corresponding to the above formula were compared to ethoxylates of various other prior art alcohols. Comparison with other vinylidene ethoxylates where the ratio of w/z is outside said range was also made. It is evident from the comparisons reported in Table 6 that only the vinylidene alcohol ethoxylates, as above represented, have a cloud point temperature within the hertofore described cloud point range of 55°C to 65°C. The importance of this particular cloud point range was hereinbefore discussed.

Accordingly, the ethoxylated $C_{11}$ to $C_{15}$ vinylidene alcohols of this invention which correspond to the above formula, wherein the ratio of w/z is in the range of about 0.685 to 0.755, demonstrate more rapid rate of solution in water, high detersive and surfactant properties, and the like, and provide cloud points within the particularly desired range. Thus, our alcohols and ethoxylate compositions are clearly distinguishable over those heretofore known. The alcohol types reported in Table 6 are those heretofore referred to in Example XVIII and Table 1.

TABLE 6

| Alcohol Type | Carbon No. Alcohol (z) | w | Ratio w/z | Cloud Point (°C.) |
|---|---|---|---|---|
| C | 11 | 8.2 | .745 | 57 |
| D | 11 | 8.2 | .745 | 74 |
| C | 11 | 9 | .818 | 77 |
| D | 11 | 9 | .818 | 82 |
| C | 13 | 9.8 | .754 | 63 |
| D | 13 | 9.8 | .754 | 80 |
| C | 13 | 10.6 | .815 | 75 |
| D | 13 | 10.6 | .815 | 87 |
| C | 15 | 10.6 | .706 | 64 |
| D | 15 | 10.6 | .706 | 78 |
| C | 15 | 13 | .866 | 87 |
| C | 15 | 13 | .866 | 95 |

EXAMPLE XXIV

To further exemplify the significance of the cloud point ranges as presented in Example XXIII, the following table lists the wetting times of the vinylidene alcohol ethoxylates of this invention compared with alcohol ethoxylates of the prior art midway between said preferred range, i.e., at a 60°C cloud point. The wetting times were performed according to the AATCC-17-1952, at 25°C as conducted in Example XXI. The alcohol types reported are the same as previously reported.

TABLE 7

| Run No. | Alcohol Type | Carbon No. Alcohol | Cloud Point, °C Ethoxylate | Wetting Time, Seconds |
|---|---|---|---|---|
| 1 | D | 11 | 60 | 9.4 |
| 2 | C | 11 | 60 | 8.5 |
| 3 | D | 13 | 60 | 12 |
| 4 | C | 13 | 60 | 8.4 |
| 5 | D | 15 | 60 | 28 |
| 6 | C | 15 | 60 | 10 |
| 7 | D | 13 | 55 | 12 |
| 8 | C | 13 | 55 | 7 |
| 9 | D | 13 | 63 | 11 |
| 10 | C | 13 | 63 | 8 |

EXAMPLE XXV

This example further demonstrates the superior wetting ability of our vinylidene alcohol ethoxylates. In particular, the following runs evidence the synergistic wetting ability of our preferred composition, i.e., the 9 to 10 mol ethylene oxide adduct of our $C_{13}$ vinylidene alcohols. Part 1 of Table 8 reports the wetting times of various prior art alcohols and of our inventive compositions at cloud points ranging from 50°C to 70°C. Part 2 of Table 8 reports the wetting times of various mixtures of alcohol ethoxylates as well as the wetting times that would be predicted from the wetting times of the individual components, alone, as reported in Part 1 of the table. The expected and actual wetting times for the various mixtures are reported. The wetting time procedure and the type alcohols employed are those as previously reported. The following runs clearly demonstrate that as little as 20 wt. % of our preferred 9 to 10 mol adduct of the $C_{13}$ vinylidene alcohols enhance the wetting ability of related vinylidene alcohols and of the prior art alcohols synergistically. A preferred composition, therefore, contains 20 to 90 wt. % of the 9 to 10 mol adduct of the $C_{13}$ vinylidene alcohol, the remainder other vinylidene ethoxylates or 5 to 15 mol ethoxylate adducts of linear primary alcohols or mixture thereof containing about 11 to 18 carbon atoms in the alcohol (alkyl) moiety. The linear primary alcohol or mixture thereof includes herein such alcohols prepared by the hydroformylation of alpha-olefins which includes about 10 to 50 wt. % alcohols having 2-lower alkyl branching.

At the various reported cloud points the mols of ethylene oxide employed with our $C_{13}$ vinylidene alcohols are as follows: the 50°C cloud point ethoxylate represents an 8.5-mol adduct; the 55°C a 9.1-mol adduct; the 60°C a 9.5-mol adduct; the 65°C a 10-mol adduct; and the 70°C a 10.2-mol adduct.

TABLE 8

| | | | Part 1 | | | | |
|---|---|---|---|---|---|---|---|
| | | | Wetting Time, Seconds Cloud Point, °C. of Alcohol Ethoxylate | | | | |
| Run No. | Alcohol Type | Carbon No. Alcohol | 50° | 55° | 60° | 65° | 70° |
| 1 | D | 11 | 5.0 | 6.25 | 8.5 | 8.75 | 8.5 |
| 2 | D | 13 | 10 | 10.6 | 12 | 12.1 | 11.5 |
| 3 | C | 13 | 6.55 | 8.0 | 8 | 9.0 | 8.5 |
| 4 | C | 15 | 13.7 | 12.5 | 11.2 | 11.25 | 12.5 |

| | | | Part 2 | | | | |
|---|---|---|---|---|---|---|---|
| | | | Wetting Times, Seconds Expected/Actual Time Cloud Point, °C. of Alcohol Ethoxylate | | | | |
| Run No. | Alcohol Type | Carbon No. Alcohol | 50° | 55° | 60° | 65° | 70° |

TABLE 8-continued

Part 1

| Run No. | Alcohol Type | Carbon No. Alcohol | Wetting Time, Seconds Cloud Point, °C. of Alcohol Ethoxylate | | | | |
|---|---|---|---|---|---|---|---|
| | | | 50° | 55° | 60° | 65° | 70° |
| 1 | D | 11/13[a] | | | 10.1/11.3 | | |
| 2 | C | 13/15[b] | | | 9.4/9.3 | | |
| 3 | D/C | 11/15[c] | | | 9 /10 | | |
| 4 | D/C | 11/15[d] | | | 9.6/10.6 | | |
| 5 | D/C | 11/15[e] | | | 10.1/11.7 | | |
| 6 | D/C | 11/15[f] | | | 9.7/12.5 | | |
| 7 | D/C | 13[g] | | | 11.2/ 9.6 | | |
| 8 | D/C | 13[h] | | | 10.4/ 8.7 | | |
| 9 | D/C | 13[i] | | | 9.6/ 9.4 | | |
| 10 | D/C | 13[j] | | | 9.0/ 8.1 | | |
| 11 | D/C/C[k] | 11/13/15[k] | 7.4 | 8.2 | 8.84/8 | 9.35 | 9.3 |
| | | | 8.0 | 8.1 | | 8.7 | 10 |
| 12 | D/D/C/C[l] | 11/13/13/15[l] | 8.11 | 8.84 | 9.76/9.3 | 10.18 | 10.0 |
| | | | 8.1 | 8.7 | | 10 | 11.2 |

[a] 54:46 wt.% mixture
[b] 57:43 wt.% mixture
[c] 80:20 wt.% mixture
[d] 60:40 wt.% mixture
[e] 40:60 wt.% mixture
[f] 20:80 wt.% mixture
[g] 80:20 wt.% mixture
[h] 60:40 wt.% mixture
[i] 40:60 wt.% mixture
[j] 20:80 wt.% mixture
[k] 40:40:20 wt.% mixture
[l] 35:30:20:15 wt.% mixture

EXAMPLE XXVI

The alcohol ethoxylates of this invention were tested and compared for detersive performance against prior art material. Generally, the prior art material and our compositions performed comparably. However, with the ethoxylates of the higher carbon alcohols, i.e., $C_{17}$ and above, the compositions of this invention were decidedly superior. Ross Miles Foam Tests (ASTM D-1173-53) at .1% concentrations, conducted at 125°F likewise demonstrated that our compositions were comparable with prior art materials.

The preceding examples can be repeated with similar success by substituting the generically and specifically described reactants and conditions of this invention for those employed in the preceding examples. Various modifications of this invention can be made or followed in light of this disclosure and the discussion herein set forth without departing from the spirit or the scope thereof.

We claim:

1. An alcohol represented by the formula:

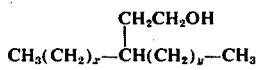

wherein, individually, $x$ and $y$ are numbers from 3 to 9 and the sum of $x$ and $y$ is a number from 8 to 16.

2. An alcohol of claim 1 selected from the group consisting of 3-butylnonanol, 3-pentyloctanol, 3-hexylnonanol, 3-butylundecanol, 3-hexyl-undecanol, 3-decylnonanol and 3-octylundecanol.

* * * * *